United States Patent
Zberg et al.

(10) Patent No.: US 9,345,819 B2
(45) Date of Patent: May 24, 2016

(54) MARKER ALLOY

(75) Inventors: Bruno Zberg, Altdorf (CH); Bodo Gerold, Zellingen (DE); Joerg Loeffler, Zurich (CH)

(73) Assignee: BIOTRONIK VI PATENT AG, Baar (CH)

( * ) Notice: Subject to any disclaimer, the term of this patent is extended or adjusted under 35 U.S.C. 154(b) by 1095 days.

(21) Appl. No.: 13/164,666

(22) Filed: Jun. 20, 2011

(65) Prior Publication Data

US 2011/0311456 A1  Dec. 22, 2011

Related U.S. Application Data

(63) Continuation-in-part of application No. 11/834,713, filed on Aug. 7, 2007, now abandoned.

Foreign Application Priority Data

Aug. 7, 2006 (DE) .......................... 10 2006 038 237

(51) Int. Cl.

| | | |
|---|---|---|
| *C22C 23/06* | (2006.01) | |
| *A61L 31/18* | (2006.01) | |
| *A61L 31/02* | (2006.01) | |
| *A61L 31/08* | (2006.01) | |
| *A61L 31/14* | (2006.01) | |

(52) U.S. Cl.
CPC ............... *A61L 31/18* (2013.01); *A61L 31/022* (2013.01); *A61L 31/088* (2013.01); *A61L 31/148* (2013.01)

(58) Field of Classification Search
CPC ....................................................... C22C 23/06
USPC ........................................................ 420/416
See application file for complete search history.

(56) References Cited

U.S. PATENT DOCUMENTS

| | | | |
|---|---|---|---|
| 3,391,034 A | | 7/1968 | London et al. |
| 2004/0241036 A1 | * | 12/2004 | Meyer-Lindenberg et al. ............................ 420/405 |
| 2006/0052863 A1 | | 3/2006 | Harder et al. |
| 2007/0191708 A1 | | 8/2007 | Gerold et al. |

FOREIGN PATENT DOCUMENTS

| | | |
|---|---|---|
| DE | 10325678 A1 | 12/2004 |
| DE | 10361942 A1 | 7/2005 |
| DE | 102005003188 A1 | 7/2006 |
| EP | 1270023 A2 | 1/2003 |
| EP | 1632256 A2 | 3/2006 |
| WO | 2005065737 A1 | 7/2005 |
| WO | 2005089664 A1 | 9/2005 |

OTHER PUBLICATIONS

Agarwal et al.; Calorimetric measurements of liquid La—Mg, Mg—Yb and Mg—Y alloys; Journal of Alloys and Compounds, vol. 217; 1995; pp. 59-64.
Hehmann et al.; Extension of Solid Solubility in Magnesium by Rapid Solidification; Materials Science and Engineering; 1990; pp. 249-265.
Rokhlin; Magnesium Alloys Containing Rare Earth Metals; Taylor & Francis; Published 2003; ISBN 0-415-28414-7; pp. 57, 78 and 79.
Search Report for European Patent Application No. 07013428.3; Jan. 22, 2008.
Search Report for German Patent Application No. 10 2006 038 237.4; May 3, 2007.

\* cited by examiner

*Primary Examiner* — Roy King
*Assistant Examiner* — Christopher Kessler
(74) *Attorney, Agent, or Firm* — Greer, Burns & Crain, Ltd.

(57) ABSTRACT

A marker alloy foreign implant made of a biodegradable metallic material and having the composition $Mg_xYb_yM_z$ wherein x is equal to 10-60 atomic percent; y is equal to 40-90 atomic percent; z is equal to 0-10 atomic percent; M is one or more element selected from the group consisting of Ag, Zn, Au, Ga, Pd, Pt, Al, Sn, Ca, Nd, Ba, Si, and Ge; and wherein x, y, and z, together, and including contaminants caused by production, result in 100 atomic percent.

15 Claims, 5 Drawing Sheets

MARKER ALLOY

CROSS-REFERENCE TO RELATED APPLICATION AND PRIORITY CLAIM

This application is a continuation-in-part of copending U.S. patent application Ser. No. 11/834,713, filed Aug. 7, 2007, entitled MARKER ALLOY, which claims priority to German Patent Application No. 10 2006 038 237.4, filed Aug. 7, 2006, and which is commonly assigned to the assignee of the present application, the disclosures of which are incorporated by reference in their entirety herein.

FIELD

The present disclosure relates to a marker alloy for an implant made of a biodegradable metallic material and its use and a method for manufacturing the marker alloy.

BACKGROUND

Implants have found uses in modern medical technology in manifold embodiments. They are used, for example, for supporting vessels, hollow organs, and duct systems (endovascular implants), for attaching and temporarily fixing tissue implants and tissue transplants, and for orthopedic purposes, for example, as nails, plates, or screws. Frequently, only a temporary support and/or retention function is necessary or desired until completion of the healing process or stabilization of the tissue. To avoid complications which result from the implants remaining permanently in the body, the implants must either be operatively removed or the implants must contain a material which is gradually degraded in the body, i.e., the material is biocorrodible. The number of biocorrodible materials based on polymers or alloys is growing continuously. Thus, inter alia, biocorrodible metal alloys of the elements is magnesium, iron, and tungsten are known.

European Patent Application No. 1 270 023 describes a magnesium alloy which is suitable for endovascular and orthopedic implants. The alloy may contain up to 5 weight-percent rare earth elements. The biocorrodible metal alloys and polymers for medical implants known in the art have the disadvantage, however, that the biocorrodible metal alloys and polymers are not visible or are not visible to a satisfactory extent in the current x-ray methods. However, x-ray diagnosis is an important instrument precisely for postoperative monitoring of the healing progress or for checking minimally-invasive interventions. Thus, for example, stents have been placed in the coronary artery during acute myocardial infarction treatment for some years. Currently, a catheter which carries the stent in an unexpanded state is positioned in the area of the lesion of the coronary vascular wall. Subsequently, the stent either expands by self-expanding forces or by inflation of a balloon to prevent obstruction of the vascular wall in the expanded state. The procedure of positioning and expanding the stent must be continuously monitored by the cardiologist during the procedure.

X-rays in the energy range from 60 to 120 keV are typically employed in the medical field for use on the heart, typically, but not exclusively, in the range from 80 to 100 keV. Because the x-ray absorption coefficient is strongly dependent on the energy, the operating range is to be considered when selecting suitable marker materials. The absorption (intensity attenuation) of the x-rays may be described in simplified form using an exponential attenuation law.

$$\frac{I}{I_0} = \exp\left[-\left(\frac{\mu}{\rho}\right)x\right]$$

In the equation above, I is the measured intensity after the sample passage, $I_0$ is the intensity of the radiation before the sample passage, $\mu/\rho$ is the mass absorption coefficient, to and x is the mass thickness of the sample. x may be calculated as the thickness t times the density of the material $\rho$, $x=\rho*t$. For alloys, the mass absorption coefficient is calculated by adding the components.

In the event of low absorption of the selected material in a given energy range of the x-ray absorption, improvement of the x-ray visibility may thus be achieved by increasing the is material thickness; however, this measure rapidly reaches its limits, in particular, when marking filigree structures, as exists in stents.

Therefore, equipping implants with a marker in the form of a coating, a strip, an inlay, or a different type of design to improve the x-ray visibility is known. For example, metal strips made of gold or other noble metals are attached in specific areas of a stent.

German Patent Application No. 103 61 942 A1 describes a radiopaque marker for medical implants, which contains 10 to 90 weight-percent of a biocorrodible base component, in particular, from the group of elements consisting of magnesium, iron, and zinc. Furthermore, the marker contains 10 to 90 weight-percent of one or more radiopaque elements from the group consisting of I, Au, Ta, Y, Nb, Mo, Ru, Rh, Ba, La, Ce, Pr, Nd, Sm, Eu, Gd, Tb, Dy, Ho, Er, Tm, Yb, Lu, Hf, Ta, W, Re, Os, and Bi as a marker component. The markers described are suitable in principle for use in biocorrodible implants, in particular, those made of biocorrodible magnesium alloys.

In implants made of biocorrodible metallic materials based on magnesium, iron, or tungsten, there are usually further requirements for the marker material:

the marker is not to be separated early from the main body of the implant by the corrosive processes, to avoid fragmentation and thus the danger of embolization;

the marker is not to degrade more rapidly than the main body, in order to still remain visible in later examination; however, at least partial in vivo degradation is to be provided;

the marker is to have sufficient x-ray density even at low material thicknesses; and the marker material is to have no or only slight influence on the degradation of the main body.

However, when markers made of metallic materials are used on biocorrodible metallic main bodies, the special problem arises that, because of electrochemical interactions between the two materials, the degradation of the main body changes in a contact area between marker and main body, and is typically accelerated. Furthermore, processing of the marker material is made more difficult because of the melting point of the base material, which is frequently low; processing methods such as soldering or laser welding, or also the immersion of the implant in a melt made of the marker material, are typically not possible.

SUMMARY

The present disclosure provides several exemplary embodiments of the present invention.

One aspect of the present disclosure provides a marker alloy for an implant made of a biodegradable metallic material, comprising an alloy of the composition MgxYbyMz wherein x is equal to 10-60 atomic percent; y is equal to 40-90 atomic percent; z is equal to 0-10 atomic percent; M is one or more element selected from the group consisting of Ag, Zn, Au, Ga, Pd, Pt, Al, Sn, Ca, Nd, Ba, Si, and Ge; and x, y, and z, together, and including contaminants caused by production, result in 100 atomic percent.

Another aspect of the present disclosure provides a method for producing an x-ray marker for an implant made of a biodegradable magnesium alloy, the method comprising (a) providing a marker alloy having the formula MgxYbyMz wherein x is equal to 10-60 atomic percent; y is equal to 40-90 atomic percent; z is equal to 0-10 atomic percent; M is one or more element selected from the group consisting of Ag, Zn, Au, Ga, Pd, Pt, Al, Sn, Ca, Nd, Ba, Si, and Ge; and x, y, and z, together, and including contaminants caused by production, result in 100 atomic percent; and (b) forming an x-ray marker for an implant made of a biodegradable magnesium alloy incorporating the marker alloy of step (a).

A further aspect of the present disclosure provides an implant incorporating a marker alloy, comprising a composition having the formula MgxYbyMz wherein x is equal to 10-60 atomic percent; y is equal to 40-90 atomic percent; z is equal to 0-10 atomic percent; M is one or more element selected from the group consisting of Ag, Zn, Au, Ga, Pd, Pt, Al, Sn, Ca, Nd, Ba, Si, and Ge; and x, y, and z, together, and including contaminants caused by production, result in 100 atomic percent.

DETAILED DESCRIPTION

Figure 1:
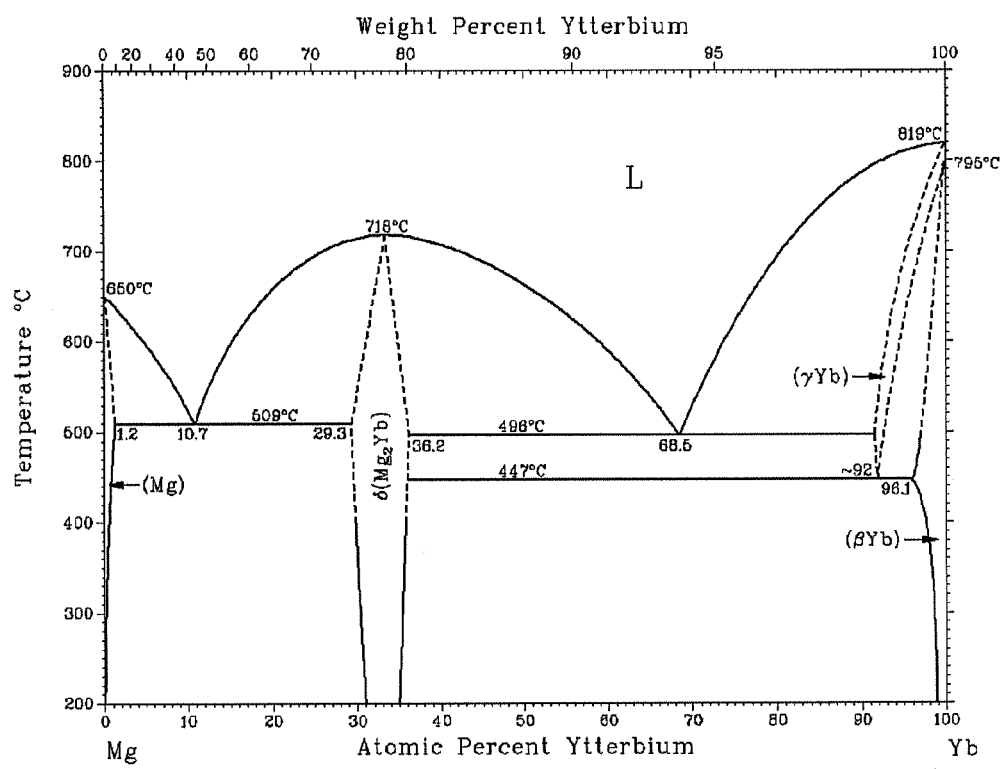
FIG. 1 shows a Mg—Yb system having two eutectic compositions.

According to one exemplary embodiment, the marker alloy is distinguished by (i) its low melting point (approximately 450° C. to 800° C. for the specified alloy compositions) and special suitability for typical thermal processing methods, such as soldering or laser welding, (ii) a homogeneous microstructure without intermetallic phases, which simplifies processability, and (iii) (at least partial) biocorrodibility. Both a homogeneous structure (mixed crystal) and the occurrence of intermetallic phases may be controlled by suitable selection of the production parameters. The production parameters essentially include, but are not limited to, the composition of the melt, the temperature of the marker melt and of the substrate, the surrounding atmosphere (inert, e.g., vacuum or argon gas; reactive, e.g., nitrogen) and pressure, and the cooling rate and further following heat treatment measures, which are, in turn, essentially characterized by the temperature and heating and cooling rates and the surrounding atmosphere.

In one embodiment, x equals 25 to 40 atomic percent and y equals 60 to 75 atomic percent, and in another embodiment x equals 28 to 35 atomic percent and y equals 65 to 72 atomic percent. Particularly, in a specific embodiment, the marker alloy corresponds to the composition Mg31,5Yb68,5. It has been shown that marker alloys of the cited compositions have a sufficiently high mean mass absorption coefficient for the medical technology x-ray energy range of 80 keV to 100 keV and a melting temperature which is below the melting point of the biocorrodible magnesium alloys used up to this point for the main body of the implant. Furthermore, marker alloys of the cited composition are also stable for a sufficiently long time in aqueous or physiological solution for the intended purposes.

The addition of the component M is optional and is particularly used for lowering the melting point of the outlet. In one specific embodiment, z equals 3 to 8 atomic percent.

The alloy composition Mg31,5Yb68,5 is a eutectic mixture, whose melting point is approximately 496° C., while, for example, the biocorrodible magnesium alloy WE43 has a melting point of approximately 590° C. A required material thickness of 51 µm for an attenuation of the intensity to the factor 0.86 may be calculated from the density of this marker alloy (5.9 g/cm$^3$) and its mean mass absorption coefficient in the energy range from 80 to 100 keV (5.98 cm2/g). This value is significantly less than the wall thickness of typical magnesium stents. The cited factor corresponds to an attenuation coefficient as is observed in gold-coated steel stents, a thickness of the steel being 70 µm and a thickness of the gold coating being 14 µm. In other words, a material thickness of the marker alloy was calculated which is necessary to obtain the same intensity attenuation as in the steel/gold composite and the ascertained value of 51 µm illustrates that this marker alloy is suitable for the filigree structures of stents.

A special feature of the marker alloy is that the electronegativity of ytterbium is less than that of magnesium, so that an acceleration of the corrosion of the main body in the contact area to the marker material by the formation of local elements is prevented.

The biocorrodible metallic material can be, but is not exclusively, a biocorrodible alloy selected from the group of elements consisting of magnesium, iron, and tungsten, in particular, a biocorrodible magnesium alloy, such as WE43. The cited elements are provided in the alloy as the main component, i.e., the mass proportion is greatest in comparison to the other elements present in the alloy. The mass proportion of the cited elements in the biocorrodible alloys can be more than 50 weight-percent, in particular, more than 70 weight-percent.

A biocorrodible magnesium alloy of the composition rare earth metals 5.2-9.9 weight-percent, yttrium 3.7-5.5 weight-percent, and the remainder less than 1 weight-percent, magnesium making up the proportion of the alloy to 100 weight-percent, is especially suitable as the implant material. This magnesium alloy has already confirmed its special suitability experimentally and in initial clinical trials, i.e., the magnesium alloy displays a high biocompatibility, favorable processing properties, good mechanical characteristics, and corrosion behavior adequate for the intended uses. For purposes of the present disclosure, the collective term "rare earth metals" includes scandium (21), yttrium (39), lanthanum (57) and the 14 elements following lanthanum (57), namely cerium (58), praseodymium (59), neodymium (60), promethium (61), samarium (62), europium (63), gadolinium (64), terbium (65), dysprosium (66), holmium (67), erbium (68), thulium (69), ytterbium (70), and lutetium (71).

The biocorrodible alloys of the elements magnesium, iron, or tungsten are to be selected in composition in such a way that the elements are biocorrodible. For purposes of the present disclosure, alloys are referred to as biocorrodible when degradation occurs in a physiological environment, which finally results in the entire implant or the part of the implant made of the material losing its mechanical integrity. Artificial plasma, as has been previously described according to EN ISO 10993-15:2000 for biocorrosion assays (composition NaCl 6.8 g/l, CaCl2 0.2 g/l, KCl 0.4 g/l, MgSO4 0.1 g/l, NaHCO3 2.2 g/l, Na2HPO4 0.126 g/l, NaH2PO4 0.026 g/l), is used as a testing medium for testing the corrosion behavior of an alloy under consideration. For this purpose, a sample of the alloy to be assayed is stored in a closed sample container with a defined quantity of the testing medium at 37° C. At time intervals, tailored to the corrosion behavior to be expected, of a few hours up to multiple months, the sample is removed and examined for corrosion traces by techniques known to those skilled in the art. The artificial plasma according to EN ISO 10993-15:2000 corresponds to a medium similar to blood and represents a possibility for reproducibly simulating a physiological environment.

The x-ray marker is provided in one specific embodiment as a solid material. Alternatively, the x-ray marker may also be embedded as a powder in an inorganic carrier matrix.

The implant is a stent, in particular, made of a magnesium or iron alloy (e.g., the magnesium alloy WE43). There is a significant need for marker materials, which result from the special requirements for the design and material of the stent.

In an exemplary embodiment, the implant is produced from the marker material.

Adding one or more of Pt, Au, Pd leads to a decrease of the melting point.

One embodiment includes an improved biodegradable amorphous alloys. Therefore, eutectic Mg-systems of biological harmless elements with low melting points were searched.

For an alloy with high density, an additional requirement was needed for the alloying elements, namely, that they also should be heavy elements. Surprisingly, only two systems, Mg—Yb and Mg—Eu, provided that profile. However, the Mg—Eu system could not be used because of its high susceptibility to corrosion. To further increase the x-ray visibility, biological harmless (already used in implants) and heavy elements like Au, Pd and Pt were used with specific embodiments. Surprisingly, with the addition of Au, Pd and Pt while maintaining the Mg—Yb ratio at 1:2.17 a further increase of the density and a further reduction of the melting point at the same time was achieved.

Figure 2:
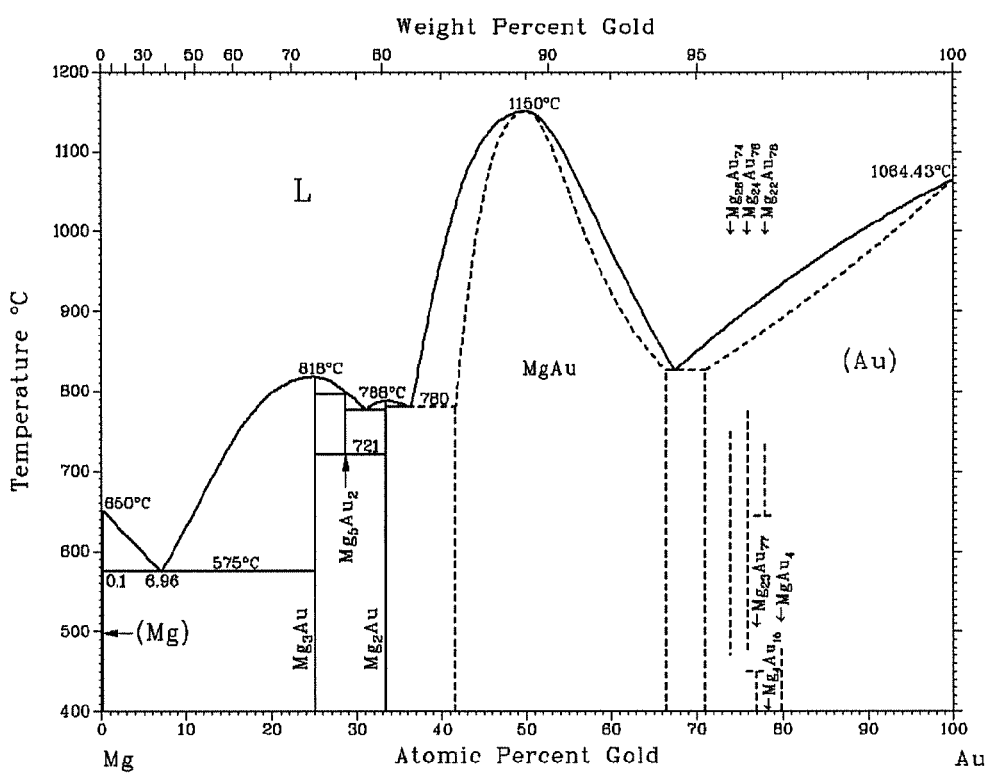
FIG. 2 shows a Mg—Au system having two eutectic compositions.
Figure 3:
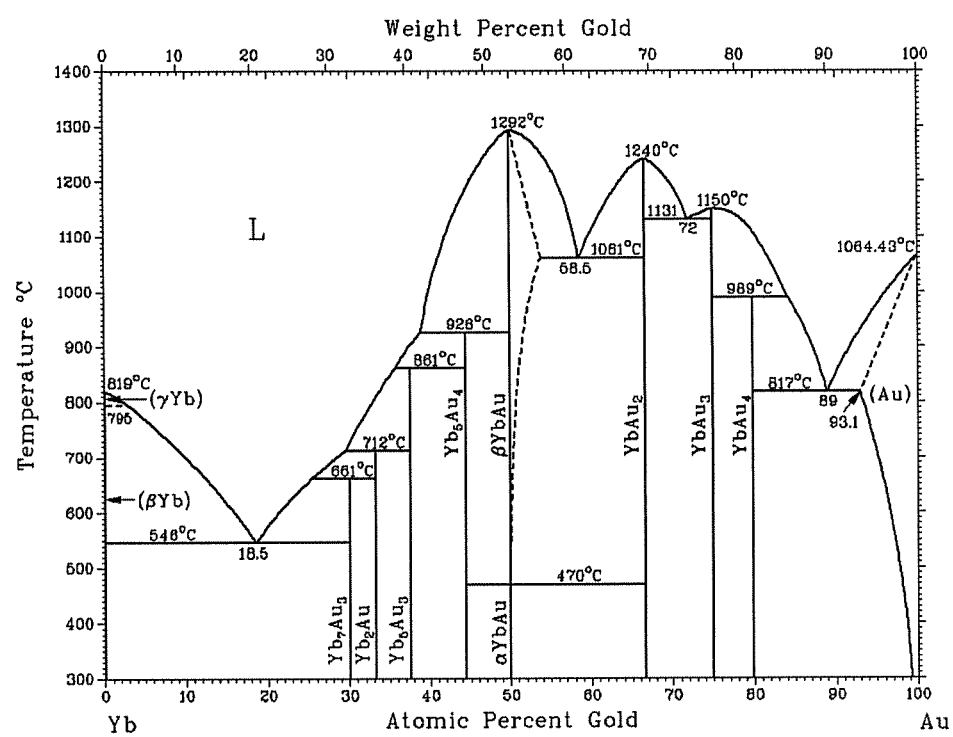
FIG. 3 shows a Yb—Au system having two eutectic compositions.

The binary phase diagrams are engineering standard tools of material developers. They allow the engineer to give educated guesses regarding expected phases or temperature ranges in ternary and higher systems. The Mg—Yb system has two eutectic compositions. As shown in FIG. 1, there is one with 68.5 At % (496° C.) and one with 10.7 At % (509° C.) Yb in Mg. As shown in FIGS. 2 and 3, the Mg—Au and Yb—Au systems also have two eutectic compositions with the lowest in terms of temperature at 6.96 At % (575° C.) for Au in Mg and at 18.5 At % (546° C.) for Au in Yb. The Mg—Yb system was the more desired system for use with specific embodiments.

Although the addition of minor amounts of the respective other element leads to a decrease of the melting point, a person skilled in the art can only speculate with a low degree of certainty that the combination of three elements Mg—Yb-(at least one of Au, Pt, and Pd) would lead to a decrease of the melting point below the lowest melting point of the binary systems (509° C.). Moreover, the ranges of compositions similarly cannot be predicted with any meaningful degree of certainty.

A lower melting point reduces the th further reduce the thermal stress which is beneficial when repeated dipping is used to coat or laminate the device.

It is also advantageous that the temperature of the melt can be increased while still remaining relatively low to improve the free flow of the melt. This makes is easier if the alloy is used as solder to attach structural elements such as other markers elements, for example, discs from Au or Ta or reservoirs for drug delivery. In particular, the free flow properties of the melts can be adjusted in a way that infiltration of cavities becomes easier and more complete.

The low melting point also allows getting finer and eventually partly amorphous or even amorphous microstructures because of the smaller solidification interval and the therefore rapid solidification. Finer microstructures provide better mechanical properties, in particular more ductility which reduces the brittleness of the marker alloy.

It was surprising that there are only two systems, Mg—Yb and Mg—Eu, that fulfilled the requirements of being degradable and radio-opaque, consisting of biocompatible elements and having a low melting point. It was even more surprising that only the Mg—Yb-system provided a reasonable electrochemical stability in air and aqueous electrolytes. And finally it was surprising that an even more radio-opaque material with even lower melting point could be achieved by alloying the Mg—Yb eutectic with the heavy biological harmless elements Au, Pd and Pt while maintaining the eutectic ratio of Mg and Yb (1:2.17).

A feature of the present material is that it is possible to produce amorphous marker alloys/metals made of this composition. With the right rapid solidification/production method (e.g., melt spinning) we can produce amorphous splats or wires that could be also used as markers when attached to the device by, for example, a biodegradable adhesive.

EXAMPLES

Example 1

3-8 At % was used for assembling the marker alloys for the implants because below 3 At % no substantial increase of density was obtained, as can be seen from the densities for Mg—Yb—Au in the following Table 1. There is actually no significant increase of the density with the addition of even 8 At % Au, Pt or Pd and therefore no significant increase of the x-ray visibility because the heavy Yb dominates over all other alloying elements. The melting point reduction is also expected to be negligible.

TABLE 1

| | Alloy | Melting point (° C.) | Density (At %) |
|---|---|---|---|
| 1 | WE43 | 545 | 1.84 |
| 2 | $Mg_{31.5}$—$Yb_{68.5}$ | 506 | 5.88 |
| 3 | $Mg_{31}$—$Yb_{68}Au_1$ | | 5.95 |
| 4 | $Mg_{30.5}$—$Yb_{66.2}$—$Au_{3.3}$ | 477 | 6.09 |
| 5 | $Mg_{30}Yb_{65}Au_5$ | | 6.20 |
| 6 | $Mg_{29}Yb_{63}Au_8$ | | 6.40 |
| 7 | $Mg_{30.5}$—$Yb_{66.2}$—$Pd_{3.3}$ | 465 | 5.96 |
| 8 | $Mg_{30.5}$—$Yb_{66.2}$—$Pt_{3.3}$ | 486 | 6.10 |

Above 8 At %, one of ordinary skill in the art may expect an increase in the melting point at least in the Mg—Yb—Au system because of the eutectic at 6.96 At % Au in the binary Yb—Au system (see Table 1 lines 3-6). In addition the brittleness due to intermetallic phases and the susceptibility to corrosion would increase considerably and the biological tolerance limits to Au, Pd, Pt (particles) may be exceeded.

FIGS. 4-7 show graphs of temperature versus heat flow for four different compositions (as noted in each graph). The upper line in each is the cooling plot and the lower line in each is the heating plot.

Figure 4:
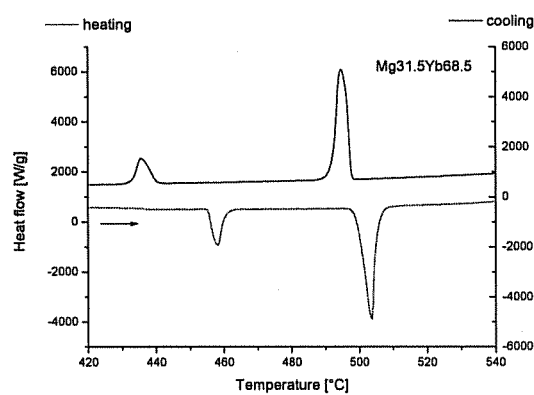
FIG. 4 shows differential scanning calorimetry data in connection with Mg31.5Yb68.5.

FIG. 4 shows differential scanning calorimetry data in connection with Mg31.5Yb68.5. As can be seen, the melting point is about 506° C.

Figure 5:
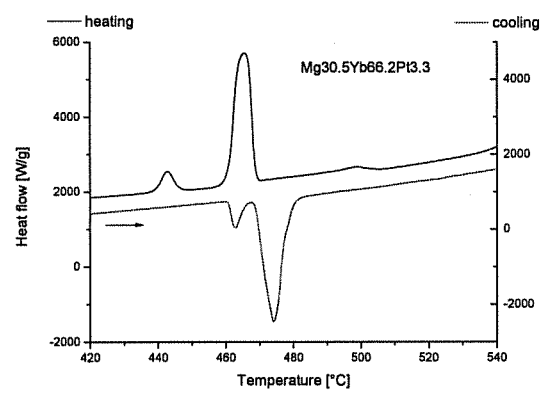
FIG. 5 shows differential scanning calorimetry data in connection with Mg30.5Yb66.2Au3.3.

FIG. 5 shows differential scanning calorimetry data in connection with Mg30.5Yb66.2Au3.3. As can be seen, the melting point is about 477° C. The presence of Au in the alloy lowers the melting point and the eutectic point of the alloy.

Figure 6:
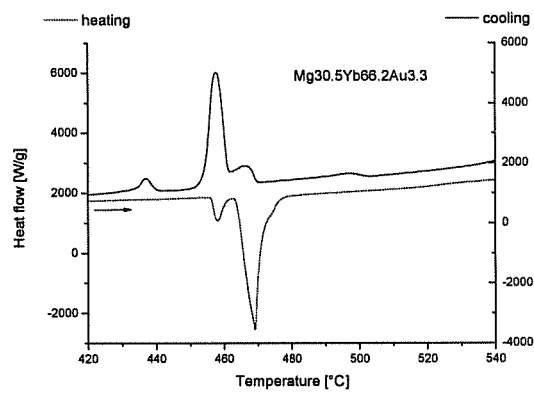
FIG. 6 shows differential scanning calorimetry data in connection with Mg30.5Yb66.2Pt3.3.

FIG. 6 shows differential scanning calorimetry data in connection with Mg30.5Yb66.2Pt3.3. As can be seen, the melting point is about 486° C. The presence of Pt in the alloy lowers the melting point and the eutectic point of the alloy.

Figure 7:
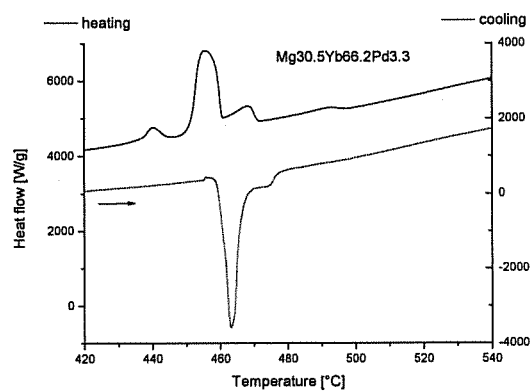
FIG. 7 shows differential scanning calorimetry data in connection with Mg30.5Yb66.2Pd3.3.

FIG. 7 shows differential scanning calorimetry data in connection with Mg30.5Yb66.2Pd3.3. As can be seen, the melting point is about 465° C. The presence of Pd in the alloy lowers the melting point and the eutectic point of the alloy.

Example 2

An alloy was produced by joint melting the alloy components in a graphite or boron nitride crucible, concretely by joint melting of 31.5 atomic percent magnesium and 68.5 atomic present ytterbium. Because both magnesium and ytterbium have a very high tendency to oxidize and low vaporization enthalpies, the melting process was performed under protective gas and with slight overpressure.

Example 3

A stent made of the magnesium alloy WE43 (containing 93 weight-percent magnesium, 4 weight-percent yttrium (W) and 3 weight-percent rare earth metals besides yttrium (E)) was immersed on both sides at the ends up to a depth of approximately 1 mm and for 1-2 seconds in a melt made of Mg31.5Yb68.5 and was subsequently cooled. The cooled layer made of the marker material was approximately 50 μm thick.

All patents, patent applications and publications referred to herein are incorporated by reference in their entirety.

What is claimed is:

1. A marker alloy for an implant made of a biodegradable metallic material, comprising:
   a marker alloy of the composition MgxYbyMz wherein
   x is equal to 10-60 atomic percent;
   y is equal to 40-90 atomic percent;
   z is equal to 3-8 atomic percent;
   M is one or more elements selected from the group consisting of Ag, Zn, Ga, Pd, Pt, Al, Sn, Ca, Si, and Ge; and wherein
   x, y, and z, together, and including contaminants caused by production, result in 100 atomic percent.

2. The marker alloy of claim 1, wherein
   x equals 25-40 atomic percent; and
   y equals 60-75 atomic percent.

3. The marker alloy of claim 2, wherein
   x equals 28-35 atomic percent; and
   y equals 65-72 atomic percent.

4. The marker alloy of claim 3, wherein the marker alloy comprises Mg30.5Yb66.2M3.3.

5. The marker alloy of claim 1, wherein the biodegradable metallic material of the implant is an alloy of an element selected from the group consisting of magnesium, iron, and tungsten.

6. The marker alloy of claim 1 wherein the implant is made of a biodegradable metallic material, comprising:
   5.2-9.9wt. % of at least one rare earth metal selected from the group consisting of scandium, lanthanum, cerium, praseodymium, neodymium, promethium, samarium, europium, gadolinium, terbium, dysprosium, holmium, erbium, thulium, ytterbium and lutetium;
   3.7-5.5 wt. % yttrium;
   less than 1 wt. % contaminants caused by production; and,
   the balance up to 100 wt. % being magnesium.

7. The alloy as claimed in claim 1, wherein the ratio of Mg to Yb is about 1:2.17.

8. The alloy as claimed in claim 1, wherein M is an element selected from the group consisting of Ag, Pd, and Pt.

9. An x-ray marker for an implant comprising the marker alloy of claim 1.

10. An implant incorporating the marker alloy of claim 1.

11. The implant of claim 10, wherein
    x equals 25-40 atomic percent; and
    y equals 60-75 atomic percent.

12. The implant of claim 11, wherein
    x equals 28-35 atomic percent; and
    y equals 65-72 atomic percent.

13. The implant of claim 12, having the marker alloy composition Mg30.5Yb66.2M3.3.

14. The implant of claim 10, wherein the biodegradable metallic material of the implant is an alloy of an element selected from the group consisting of magnesium, iron, and tungsten.

15. The implant of claim 10, wherein the implant is a stent.

* * * * *